(12) United States Patent
Keller et al.

(10) Patent No.: US 11,278,347 B2
(45) Date of Patent: *Mar. 22, 2022

(54) ELECTROSURGICAL DEVICES INCLUDING TRANSVERSE ELECTRODE CONFIGURATIONS

(71) Applicant: Covidien LP, Mansfield, MA (US)

(72) Inventors: Craig A. Keller, Boulder, CO (US); Guillaume Lessard, Louisville, CO (US); Richard M. Ferrell, Alexandria, VA (US)

(73) Assignee: Covidien LP, Mansfield, MA (US)

( * ) Notice: Subject to any disclaimer, the term of this patent is extended or adjusted under 35 U.S.C. 154(b) by 993 days.

This patent is subject to a terminal disclaimer.

(21) Appl. No.: 15/971,853

(22) Filed: May 4, 2018

(65) Prior Publication Data

US 2018/0250067 A1 Sep. 6, 2018

Related U.S. Application Data

(63) Continuation of application No. 14/559,273, filed on Dec. 3, 2014, now Pat. No. 10,058,377.

(Continued)

(51) Int. Cl.
*A61B 18/14* (2006.01)
*A61B 18/12* (2006.01)
*A61B 18/00* (2006.01)

(52) U.S. Cl.
CPC ...... *A61B 18/1445* (2013.01); *A61B 18/1442* (2013.01); *A61B 2018/0063* (2013.01);
(Continued)

(58) Field of Classification Search
CPC ............ A61B 18/1442; A61B 18/1445; A61B 18/1467; A61B 2018/1467;
(Continued)

(56) References Cited

U.S. PATENT DOCUMENTS

| | | |
|---|---|---|
| D249,549 S | 9/1978 | Pike |
| D263,020 S | 2/1982 | Rau, III |

(Continued)

FOREIGN PATENT DOCUMENTS

| | | |
|---|---|---|
| CN | 201299462 Y | 9/2009 |
| CN | 102481169 A | 5/2012 |

(Continued)

OTHER PUBLICATIONS

U.S. Appl. No. 14/098,953, filed Dec. 6, 2013; inventor: Cunningham.

(Continued)

*Primary Examiner* — Eun Hwa Kim

(57) ABSTRACT

An end effector assembly for an electrosurgical device includes first and second jaw members movable between spaced-apart and approximated positions. The jaw members include tissue-contacting surfaces that define a tissue grasping area. One of the jaw members includes an electrically-insulating body, an interior electrode, and an exterior electrode. The interior electrode is positioned interiorly of outer bounds of the tissue grasping area. A portion of the interior electrode forms part of the tissue-contacting surface. The exterior electrode is positioned exteriorly of the outer bounds of the tissue grasping area. At least one portion of the exterior electrode: extends along the outer back surface of the body, is disposed within the body, and is positioned adjacent the outer bounds of the tissue grasping area. The interior and exterior electrodes are configured to conduct energy through tissue grasped within the tissue grasping area to seal tissue.

20 Claims, 7 Drawing Sheets

Related U.S. Application Data

(60) Provisional application No. 61/973,982, filed on Apr. 2, 2014, provisional application No. 61/973,991, filed on Apr. 2, 2014, provisional application No. 61/973,964, filed on Apr. 2, 2014, provisional application No. 61/973,948, filed on Apr. 2, 2014.

(52) U.S. Cl.
CPC .............. *A61B 2018/00083* (2013.01); *A61B 2018/00089* (2013.01); *A61B 2018/00767* (2013.01); *A61B 2018/00827* (2013.01); *A61B 2018/126* (2013.01); *A61B 2018/1405* (2013.01); *A61B 2018/1455* (2013.01); *A61B 2018/1467* (2013.01); *A61B 2018/1495* (2013.01)

(58) Field of Classification Search
CPC .... A61B 2018/0063; A61B 2018/1405; A61B 2018/00083; A61B 2018/00089; A61B 2018/1495; A61B 2018/126; A61B 2018/1455; A61B 2018/00767; A61B 2018/00827
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,151,102 A | 9/1992 | Kamiyama et al. |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,403,312 A | 4/1995 | Yates et al. |
| D358,887 S | 5/1995 | Feinberg |
| 5,626,578 A | 5/1997 | Tihon |
| 5,658,281 A | 8/1997 | Heard |
| D384,413 S | 9/1997 | Zlock et al. |
| 5,688,270 A | 11/1997 | Yates et al. |
| 5,766,166 A | 6/1998 | Hooven |
| H1745 H | 8/1998 | Paraschac |
| 5,810,811 A | 9/1998 | Yates et al. |
| 5,833,690 A | 11/1998 | Yates et al. |
| D402,028 S | 12/1998 | Grimm et al. |
| 5,876,401 A | 3/1999 | Schulze et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| 6,066,137 A | 5/2000 | Greep |
| 6,086,586 A | 7/2000 | Hooven |
| H1904 H | 10/2000 | Yates et al. |
| 6,162,220 A | 12/2000 | Nezhat |
| D449,886 S | 10/2001 | Tetzlaff et al. |
| 6,334,860 B1 | 1/2002 | Dorn |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,458,128 B1 | 10/2002 | Schulze |
| D465,281 S | 11/2002 | Lang |
| D466,209 S | 11/2002 | Bon |
| 6,656,177 B2 | 12/2003 | Truckai et al. |
| D493,888 S | 8/2004 | Reschke |
| 6,770,072 B1 | 8/2004 | Truckai et al. |
| 6,773,409 B2 | 8/2004 | Truckai et al. |
| D496,997 S | 10/2004 | Dycus et al. |
| D499,181 S | 11/2004 | Dycus et al. |
| D502,994 S | 3/2005 | Blake, III |
| 6,926,716 B2 | 8/2005 | Baker et al. |
| D509,297 S | 9/2005 | Wells |
| D525,361 S | 7/2006 | Hushka |
| D531,311 S | 10/2006 | Guerra et al. |
| 7,135,020 B2 | 11/2006 | Lawes et al. |
| D533,274 S | 12/2006 | Visconti et al. |
| D533,942 S | 12/2006 | Kerr et al. |
| 7,147,637 B2 | 12/2006 | Goble |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,278,992 B2 | 10/2007 | Cropper et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,419,490 B2 | 9/2008 | Falkenstein et al. |
| D582,038 S | 12/2008 | Swoyer et al. |
| 7,597,693 B2 | 10/2009 | Garrison |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,799,026 B2 | 9/2010 | Schechter et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 8,734,445 B2 | 5/2014 | Johnson et al. |
| 2002/0111624 A1 | 8/2002 | Witt et al. |
| 2003/0065348 A1* | 4/2003 | Hess ................ A61B 17/00008 606/159 |
| 2003/0199870 A1 | 10/2003 | Truckai et al. |
| 2006/0271038 A1 | 11/2006 | Johnson et al. |
| 2009/0216229 A1 | 8/2009 | Chojin |
| 2010/0179543 A1 | 7/2010 | Johnson et al. |
| 2011/0028964 A1* | 2/2011 | Edwards ............ A61B 18/1442 606/33 |
| 2012/0046662 A1 | 2/2012 | Gilbert |
| 2012/0059374 A1 | 3/2012 | Johnson et al. |
| 2013/0079764 A1 | 3/2013 | Schaller et al. |
| 2013/0185922 A1 | 7/2013 | Twomey et al. |
| 2013/0255063 A1 | 10/2013 | Hart et al. |
| 2014/0163541 A1* | 6/2014 | Shelton, IV ... A61B 17/320092 606/33 |
| 2014/0353869 A1 | 12/2014 | Goodman et al. |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |

(56) References Cited

FOREIGN PATENT DOCUMENTS

| | | |
|---|---|---|
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| DE | 102009049401 A1 | 2/2011 |
| EP | 0722696 A1 | 7/1996 |
| EP | 1281878 A1 | 2/2003 |
| EP | 1159926 A2 | 3/2003 |
| EP | 1568330 A1 | 8/2005 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | 0540112 | 2/1993 |
| JP | 0006030945 A | 2/1994 |
| JP | 6121797 A | 5/1994 |
| JP | 6285078 A | 10/1994 |
| JP | 06343644 A | 12/1994 |
| JP | 6511401 | 12/1994 |
| JP | 07265328 A | 10/1995 |
| JP | 856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 C | 1/1997 |
| JP | 09000538 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 A | 1/2001 |
| JP | 2001029355 | 2/2001 |
| JP | 2001029356 A | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Heniford et al. "Initial Research and Clinical Results with an Electrothermal Bipolar Vessel Sealer" Oct. 1999.
Partial European Search Report issued in corresponding European Patent Appln. No. 14200408 dated Aug. 24, 2015.
Extended European Search Report issued in corresponding application No. EP 14200408.4 dated Dec. 9, 2015.
Canadian office action issued in corresponding application No. 2875550 dated Feb. 1, 2016.
Australian office action issued in corresponding application No. 2014277714 dated Oct. 19, 2016.
Chinese office action issued in corresponding application No. 201410838377.4 dated Dec. 20, 2016.
Second Chinese Office Action (with English translation), issued in corresponding Chinese Application No. 201410838377.4 dated Aug. 1, 2017; 11 total pages.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).

(56) References Cited

OTHER PUBLICATIONS

Johnson et al. "Evaluation of a Bipolar Electrothermal Vessel Sealing Device in Hemorrhoidectomy" Sales/Product Literature; Jan. 2004 (1 page).
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001 pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.
U.S. Appl. No. 14/065,644, filed Oct. 29, 2013; inventor: Reschke.

\* cited by examiner

ELECTROSURGICAL DEVICES INCLUDING TRANSVERSE ELECTRODE CONFIGURATIONS

CROSS-REFERENCE TO RELATED APPLICATIONS

This application is a continuation application of U.S. patent application Ser. No. 14/559,273, filed on Dec. 3, 2014, which claims the benefit of, and priority to, U.S. Provisional Patent Application Nos. 61/973,948, 61/973,964, 61/973,982, and 61/973,991, all of which were filed on Apr. 2, 2014, the entire contents of each of which being incorporated by reference herein. This application is also related to U.S. patent application Ser. Nos. 14/558,988, 14/559,032, and 14/559,410, all of which were filed on Dec. 3, 2014, the entire contents of each of which being incorporated by reference herein.

BACKGROUND

Technical Field

The present disclosure relates to electrosurgical devices and, more particularly, to transverse electrode configurations for end effector assemblies of electrosurgical devices.

Background of Related Art

Electrosurgical devices are utilized to apply energy to tissue to achieve a desired tissue effect. Electrosurgical forceps, for example, utilize both mechanical clamping action and energy to affect hemostasis by heating tissue to coagulate and/or cauterize tissue. Certain surgical procedures require more than simply cauterizing tissue and rely on the unique combination of clamping pressure, gap distance, and energy control to "seal" tissue. Typically, energy is conducted between opposed jaw members and through tissue grasped therebetween, e.g., generally perpendicular to the plane extending between the jaw members, to seal or otherwise treat tissue. Alternatively, the jaw members may be configured such that energy is conducted transversely across the jaw members and through tissue grasped therebetween, e.g., generally parallel to the plane extending between the jaw members, to seal or otherwise treat tissue. As can be appreciated, the energy control parameters and/or physical characteristics of the end effector assembly for creating an effective tissue seal may vary depending upon whether energy is conducted between opposed jaw members or transversely relative to the jaw members.

SUMMARY

As detailed below, provided in accordance with the present disclosure are end effector assemblies that incorporate features configured to facilitate tissue sealing wherein electrosurgical energy is conducted transversely across the jaw members and through tissue grasped therebetween to seal tissue. As used herein, the term "distal" refers to the portion that is being described which is further from a user, while the term "proximal" refers to the portion that is being described which is closer to a user. Further, to the extent consistent, any of the aspects described herein may be used in conjunction with any of the other aspects described herein.

Provided in accordance with aspects of the present disclosure is an end effector assembly including first and second jaw members movable relative to one another between a spaced-apart position and an approximated position. Each jaw member includes an opposed tissue-contacting surface. The opposed tissue-contacting surfaces cooperate to define a tissue grasping area for grasping tissue therebetween when the jaw members are moved to the approximated position. One of the jaw members includes an electrically-insulating body, an interior electrode, and an exterior electrode. The body defines an outer back surface and an opposed surface that forms part of the tissue-contacting surface of the jaw member. The interior electrode is positioned interiorly of outer bounds of the tissue grasping area. At least a portion of the interior electrode forms part of the tissue-contacting surface of the jaw member. The exterior electrode is positioned exteriorly of the outer bounds of the tissue grasping area. A first portion of the exterior electrode extends along the outer back surface of the body. A second portion of the exterior electrode is disposed within the body. A third portion of the exterior electrode is positioned adjacent the outer bounds of the tissue grasping area. The interior and exterior electrodes are configured to conduct energy therebetween and through tissue grasped within the tissue grasping area to seal tissue grasped within the tissue grasping area.

In aspects, first and second ends of the exterior electrode define the third portion of the exterior electrode. In such a configuration, the first and second ends of the exterior electrode are disposed adjacent opposite outer boundaries of the tissue grasping area, e.g., on either side of the tissue grasping area. Further, the first and second ends of the exterior electrode may be bent back onto the exterior electrode.

In aspects, the jaw member includes chamfered exterior lateral sides.

In aspects, the interior electrode defines an increased thickness as compared to the exterior electrode.

In aspects, the exterior electrode is formed from sheet metal.

In aspects, the body of the jaw member defines a knife channel and the interior electrode is disposed within the knife channel. Further, the knife channel and the inner electrode may define generally "U"-shaped configurations.

In aspects, the jaw member further includes an electrically-conductive support member disposed in contact with the exterior electrode. The support member may include a portion that extends through the body of the jaw member and/or a portion that extends along the outer back surface of the body of the jaw member.

In aspects, first and second ends of the support member are positioned adjacent respective first and second ends of the exterior electrode. In such aspects, an electrically insulating portion of the body of the jaw member is disposed between the first and second ends of the support member and the respective first and second ends of the exterior electrode.

In aspects, the tissue grasping area defines a total width of less than about 8 mm or, more particularly, less than about 6 mm.

In aspects, the other jaw member may be configured similar to the jaw member detailed above or, alternatively, may include an electrically-insulating body that defines its tissue-contacting surface. In aspects where the both the jaw members define similar configurations, the jaw members may be configured to conduct energy between the interior and exterior electrodes of both of the jaw members, e.g., from one jaw member to the other and to/from the same jaw member.

BRIEF DESCRIPTION OF THE DRAWINGS

Various aspects and features of the present disclosure are described herein with reference to the drawings wherein like reference numerals identify similar or identical elements.

DETAILED DESCRIPTION

The present disclosure provides various embodiments of end effector assemblies that incorporate features configured to facilitate tissue sealing wherein electrosurgical energy is conducted transversely across the jaw members and through tissue grasped therebetween to seal tissue. Except where specifically noted as being mutually exclusive, any of the features detailed herein below may be used in conjunction with any or all of the features detailed herein, and may be embodied in any of the exemplary embodiments provided herein, combinations thereof, or in any other suitable end effector assembly.

Figure 4:
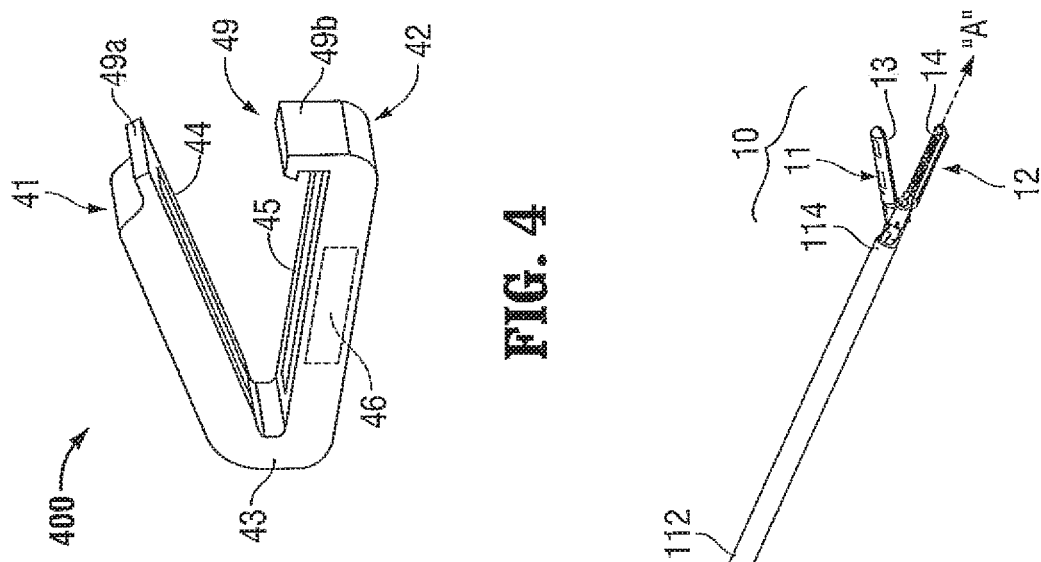
FIG. 4 is a perspective view of an electrosurgical tissue clip configured for use in accordance with the present disclosure.
Figure 1:
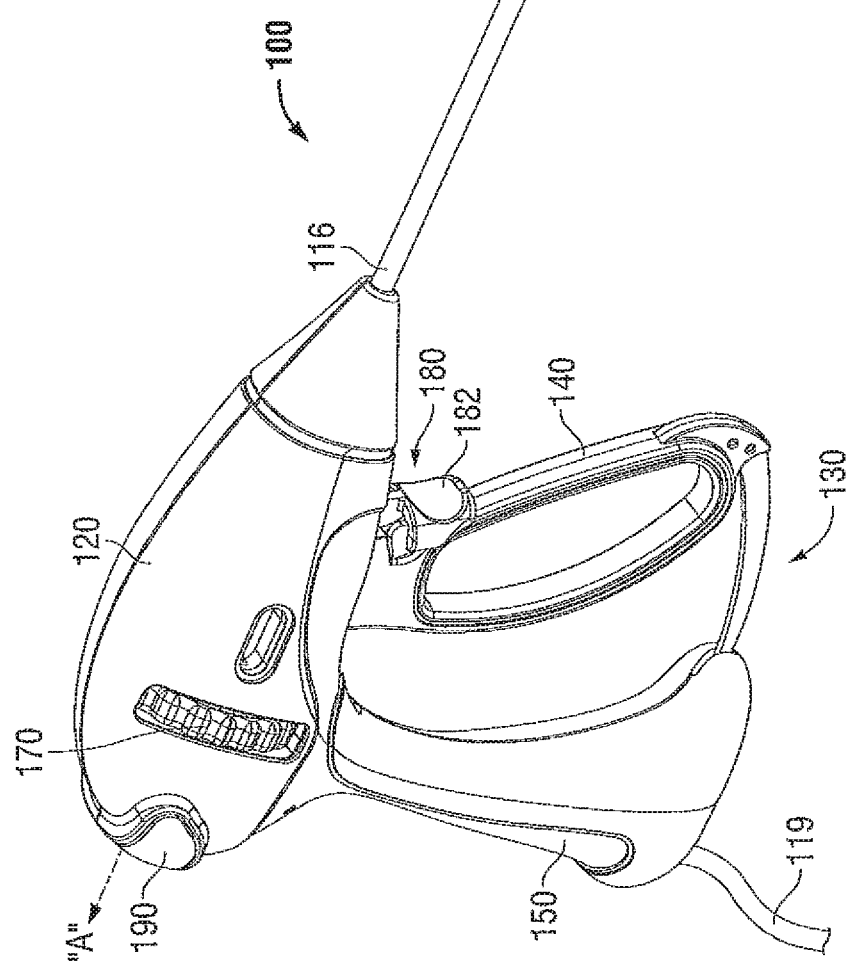
FIG. 1 is a perspective view of an endoscopic electrosurgical forceps configured for use in accordance with the present disclosure.
Figure 2:
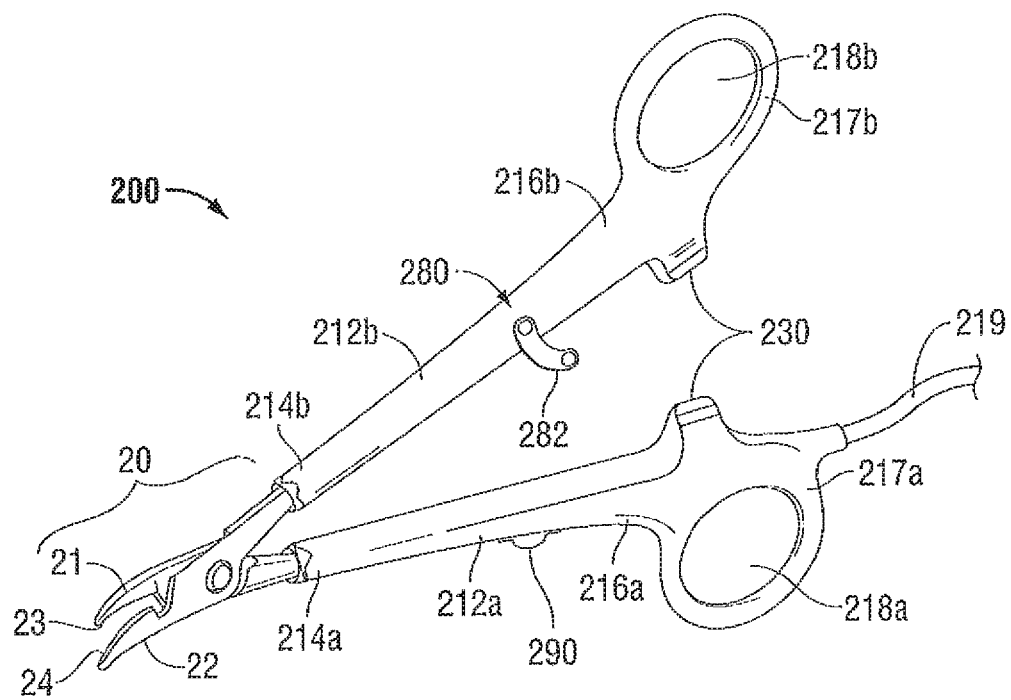
FIG. 2 is a perspective view of an open electrosurgical forceps configured for use in accordance with the present disclosure.
Figure 3:
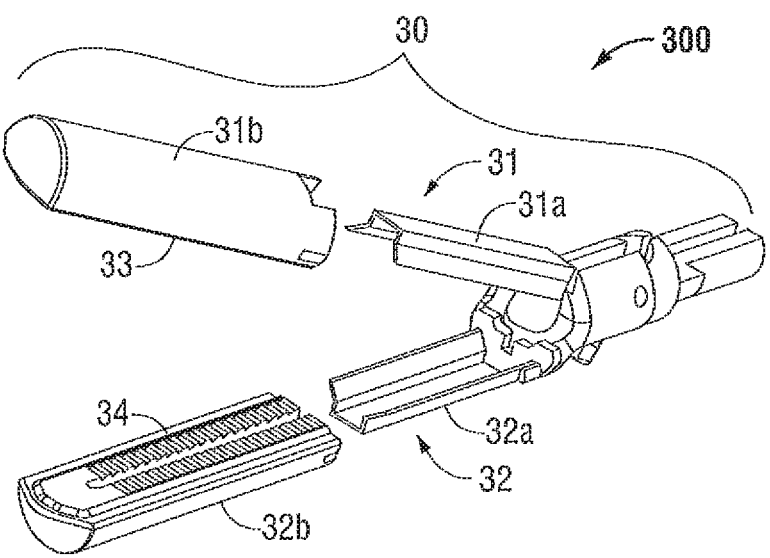
FIG. 3 is a, perspective view of the distal end of an electrosurgical forceps including reposable jaw members configured for use in accordance with the present disclosure.

Turning to FIGS. 1-4, FIG. 1 depicts an endoscopic electrosurgical forceps 100 for use in connection with endoscopic surgical procedures; FIG. 2 depicts an open electrosurgical forceps 200 contemplated for use in connection with traditional open surgical procedures; FIG. 3 depicts a reposable electrosurgical forceps 300 (which may be provided in either an endoscopic or open configuration); and FIG. 4 depicts an electrosurgical tissue clip 400. For the purposes herein, either forceps 100, forceps 200, forceps 300, clip 400, or any other suitable electrosurgical device may be utilized in implementing the aspects and features of the present disclosure. While different electrical and mechanical connections and considerations apply to each particular type of device, the aspects and features of the present disclosure detailed below and the operating characteristics thereof remain generally consistent regardless of the particular electrosurgical device used therewith.

With reference to FIG. 1, endoscopic electrosurgical forceps 100 defines a longitudinal axis "A-A" and includes a housing 120, a handle assembly 130, a rotating assembly 170, a trigger assembly 180, and an end effector assembly 10. Forceps 100 further includes a shaft 112 having a distal end 114 configured to mechanically engage end effector assembly 10 and a proximal end 116 that mechanically engages housing 120.

A cable 119 connects forceps 100 to a source of energy, e.g., an external generator (not shown), although forceps 100 may alternatively be configured as a handheld device including a portable generator (not shown) disposed within housing 120. Cable 119 includes two or more wires (not shown) that extend into and through housing 120 and shaft 112 to connect the generator (not shown) to activation button 190 and end effector assembly 10 for selectively supplying energy to end effector assembly 10.

End effector assembly 10 is shown attached at distal end 114 of shaft 112 and includes a pair of opposed jaw members 11, 12. Each jaw member 11, 12 includes a tissue-contacting surface 13, 14, respectively. One or more electrodes (not explicitly shown) is incorporated into either or both of jaw members 11, 12 and configured to conduct energy through tissue grasped between tissue-contacting surfaces 13,14 of jaw members 11, 12, respectively, to treat, e.g., seal, tissue. End effector assembly 10 is designed as a unilateral assembly, i.e., where jaw member 12 is fixed relative to shaft 112 and jaw member 11 is movable relative to shaft 112 and fixed jaw member 12. However, end effector assembly 10 may alternatively be configured as a bilateral assembly, i.e., where both jaw member 11 and jaw member 12 are movable relative to one another and to shaft 112. In some embodiments, a knife assembly (not shown) is disposed within shaft 112 and a knife channel, e.g., similar to knife channel 54 of jaw member 52 (FIGS. 5A-5B), is defined within one or both jaw members 11, 12 to permit reciprocation of a knife blade (not shown) therethrough, e.g., upon activation of trigger 182 of trigger assembly 180, to cut sealed tissue.

Continuing with reference to FIG. 1, handle assembly 130 includes a fixed handle 150 and a movable handle 140. Fixed handle 150 is integrally associated with housing 120 and movable handle 140 is movable relative to fixed handle 150. Movable handle 140 is ultimately connected to a drive assembly (not shown) that, together, mechanically cooperate to impart movement of jaw members 11, 12 between a spaced-apart position and an approximated position for grasping tissue between tissue-contacting surfaces 13, 14 of jaw members 11, 12, respectively. As shown in FIG. 1, movable handle 140 is initially spaced-apart from fixed handle 150 and, correspondingly, jaw members 11, 12 are disposed in the spaced-apart position. Movable handle 140 is depressible from this initial position to a depressed position corresponding to the approximated position of jaw members 11, 12. Rotating assembly 170 is rotatable in either direction about a longitudinal axis "A-A" to rotate end effector 10 about longitudinal axis "A-A."

Referring now to FIG. 2, open electrosurgical forceps 200 is shown including two elongated shafts 212a, 212b each having a proximal end 216a, 216b and a distal end 214a, 214b, respectively. Forceps 200 includes an end effector assembly 20 having a pair of opposed jaw members 21, 22 that are attached to distal ends 214a, 214b of shafts 212a, 212b. Each shaft 212a, 212b further includes a handle 217a, 217b disposed at the proximal end 216a, 216b thereof. Each handle 217a, 217b defines a finger hole 218a, 218b therethrough for receiving a finger of the user. As can be appreciated, finger holes 218a, 218b facilitate movement of shafts 212a, 212b relative to one another from an open position, wherein jaw members 21, 22 are disposed in spaced-apart relation relative to one another, to a closed position, wherein jaw members 21, 22 cooperate to grasp tissue therebetween.

A ratchet 230 may be included for selectively locking shafts 212a, 212b and, thus, jaw members 21, 22, at various different positions during pivoting. Ratchet 230 may include graduations or other visual markings that enable the user to easily and quickly ascertain and control the amount of closure force desired between the jaw members 21, 22.

With continued reference to FIG. 2, end effector assembly 20 is similar to end effector assembly 10 of forceps 100 (see FIG. 1). Jaw members 21, 22 of end effector assembly 20 each include a tissue-contacting surface 23, 24, respectively. Either or both of jaw members 21, 22 incorporate one or more electrodes (not explicitly shown) configured to facilitate the conduction of energy through tissue grasped between tissue-contacting surfaces 23, 24 of jaw members 21, 22, respectively, to treat, e.g., seal, tissue. A cable 219 including one or more wires (not shown) extend into and through one of the shafts, e.g., shaft 212a, is provided for connecting a generator (not shown) to activation button 290 and end effector assembly 20 for selectively supplying energy to end effector assembly 20 upon actuation of activation button 290. Similar to forceps 100 (FIG. 1), forceps 200 may further include a knife assembly (not shown) disposed within either of the shafts, e.g., shaft 212b, and a knife channel, e.g., knife channel 54 of jaw member 52 (FIGS. 5A-5B), defined within one or both jaw members 21, 22 to permit reciprocation of a knife blade (not shown) therethrough, e.g., upon activation of trigger 282 of trigger assembly 280, to cut sealed tissue.

Turning now to FIG. 3, reposable electrosurgical forceps 300 may be configured as an open forceps, e.g., similar to forceps 200 (FIG. 2), an endoscopic forceps, e.g., similar to forceps 100 (FIG. 1), or in any other suitable configuration. Reposable forceps 300 includes an end effector assembly 30 similar to end effector assemblies 10, 20 (FIGS. 1, 2, respectively), except that jaw members 31, 32 each include a fixed jaw frame 31a, 32a and a removable jaw body 31b, 32b, respectively. Jaw bodies 31b, 32b are removably engagable with respective jaw frames 31a, 32a and include tissue-contacting surfaces 33, 34, respectively. Either or both of jaw bodies 31b, 32b further incorporate one or more electrodes (not explicitly shown) configured to facilitate the conduction of energy through tissue grasped between tissue-contacting surfaces 33, 34, to treat, e.g., seal, tissue. Forceps 300 may otherwise be similar to and/or incorporate any of the features of forceps 100, 200 (FIGS. 1 and 2, respectively), detailed above.

Referring now to FIG. 4, electrosurgical tissue clip 400 is an integrated or stand-alone end effector assembly including first and second jaw members 41, 42, respectively, coupled to one another by a flexible joint 43, although jaw members 41, 42 may alternatively be coupled to one another by a hinge, pivot, or any other suitable mechanism. Flexible joint 43 permits jaw members 41, 42 to move relative to one another between spaced-apart and approximated positions for grasping tissue therebetween. Jaw members 41, 42 of tissue clip 400 each further include contacting surface 44, 45, respectively, and either or both of jaw members 41, 42 incorporate one or more electrodes (not explicitly shown) therein. A miniaturized generator 46 is disposed within one of the jaw members, e.g., jaw member 42, for selectively supplying energy to the electrodes of either or both of jaw members 41, 42 for conduction through tissue grasped between tissue-contacting surfaces 44, 45 of jaw members 41, 42, respectively, to treat, e.g., seal, tissue. That is, tissue clip 400 is a fully integrated tissue-treating unit incorporating all the necessary mechanical and electrical components for electrosurgically treating tissue. A latch mechanism 49 including first and second latch components 49a, 49b disposed on first and second jaw members 41, 42, respectively, may also be provided for selectively locking jaw members 41 and 42 relative to one another in various different positions.

Turning now to FIGS. 5A-21, various embodiments of end effector assemblies configured for use with forceps 100 (FIG. 1), forceps 200 (FIG. 2), forceps 300 (FIG. 3), tissue clip 400 (FIG. 4), or any other suitable electrosurgical device, are shown. In particular, each of the embodiments of end effector assemblies detailed hereafter is configured to facilitate electrosurgical tissue sealing using transverse current flow; that is, electrosurgical tissue sealing wherein the electrosurgical energy is conducted transversely across the jaw members and through tissue grasped therebetween to seal tissue.

Figure 5A:
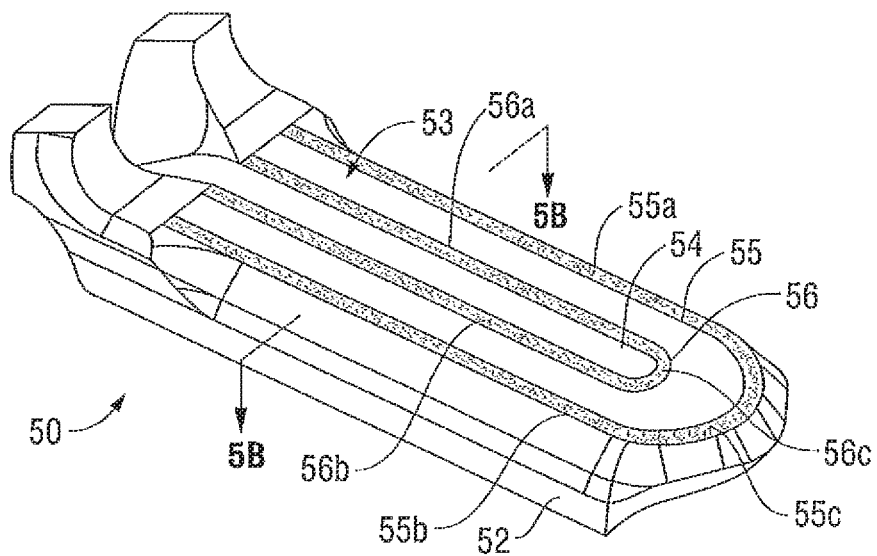
FIG. 5A is a top, perspective view of a jaw member of an end effector assembly provided in accordance with the present disclosure and configured for use with any of the above electrosurgical devices or any other suitable electrosurgical device.
Figure 5B:
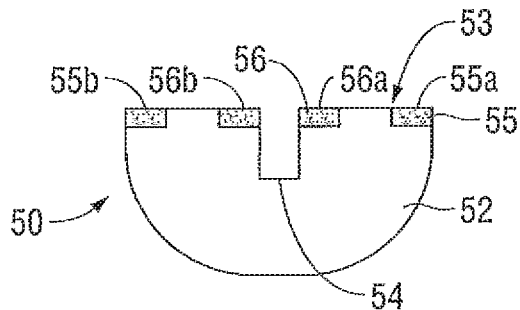
FIG. 5B is a cross-sectional view taken along section line "5B-5B" of FIG. 5A.

Referring to FIGS. 5A-5B, the distal end of one of the jaw members of an end effector assembly 50 provided in accordance with the present disclosure is shown generally identified by reference numeral 52. Although end effector assembly 50 includes a pair of jaw members that cooperate to grasp tissue therebetween, similarly as detailed above, only jaw members 52 is shown. Both jaw members of end effector assembly 50 may be similar to jaw member 52 or, alternatively, only one of the jaw members, e.g., jaw member 52, may incorporate electrodes, while the other jaw member (not shown) simply provides an opposed tissue-contacting surface that is electrically insulated, for grasping tissue between the jaw members of end effector assembly 50.

Continuing with reference to FIGS. 5A-5B, jaw member 52 is formed from an electrically insulating material and defines a tissue-contacting surface 53 having a knife channel 54 extending longitudinally therethrough. Knife channel 54 permits reciprocation of a knife blade (not shown) therethrough to cut tissue grasped between the jaw members of end effector assembly 50 after tissue has been sealed (or simply to cut the tissue where tissue sealing is not desired). Jaw member 52 further includes first and second electrodes formed as electrically-conductive plates 55, 56 disposed in the plane of tissue-contacting surface 53. Plates 55, 56 are seated within recesses defined within tissue-contacting surface 53 such that plates 55, 56 and tissue-contacting surface 53 cooperate to define a planar surface. Each plate 55, 56 defines a generally "U"-shaped configuration formed from first and second longitudinal sections 55a, 55b and 56a, 56b, respectively, interconnected by respective curved sections 55c, 56c. The radius of curvature of curved section 55c of first plate 55 is greater than that of curved section 56c of second plate 56, e.g., curved section 55c and curved section 56c define concentric arcs, enabling first plate 55 to extend about the outer periphery of tissue-contacting surface 53, while second plate 56 is positioned within first plate 55 and extends about the inner periphery of tissue-contacting surface 53, e.g., bordering knife channel 54. The width of plates 55, 56 and the spacing between plates 55, 56, which is filled via the insulated jaw member 52, is constant along the lengths of plates 55, 56.

Jaw member 52 and/or the other jaw member (not shown) of end effector assembly 50 may include one or more stop members (not shown) or other stop features, e.g., mechanical stops in the drive assembly (not shown), configured to define a minimum gap distance between the tissue-contacting surfaces of the jaw members of end effector assembly 50 of between about 0.004 inches to about 0.006 inches (about 100 μm to about 150 μm) when approximated about tissue, as it has been found that a gap distance within this range promotes formation of an effective tissue seal. Such stop members or stop features (not shown) may be molded, casted, machined, deposited (e.g., via evaporation), adhered, or otherwise disposed on the jaw members or other components to achieve a minimum gap distance within the above-noted range. The above-noted gap distances and suitable structures and/or methods for establishing the same are equally applicable for use with any of the other end effector assemblies detailed herein.

With respect to the use of end effector assembly 50, tissue is initially grasped between the jaw members of end effector assembly 50 such that a portion of tissue to be sealed is grasped within a tissue seal area defined by jaw member 52. More specifically, with sections 56a, 56b, 56c of plate 56 bordering knife channel 54 and with sections 55a, 55b, 55c of plate 55 bordering the outer periphery of the tissue-contacting surface 53 of jaw member 52, a generally "U"-shaped tissue seal area is defined between and bounded by plates 55, 56. Once tissue is grasped within this tissue seal area, first plate 55 of jaw member 52 is energized to a first electrical potential and second plate 56 of jaw member 52 is energized to a second, different electrical potential to establish an electrical potential gradient therebetween. As such, energy is conducted between plates 55, 56 and through tissue grasped within the tissue seal area to establish a tissue seal. That is, as a result of the flow of energy between plates 55, 56, tissue disposed therebetween, e.g., tissue grasped within the tissue seal area, is sealed. This configuration facilitates formation of an effective tissue seal. Further, this configuration reduces thermal spread by eliminating alternate current paths through tissue since the plates 55, 56 are positioned to bound the tissue seal area and direct the flow of energy through tissue within the tissue seal area.

Once tissue has been sealed as detailed above, and if desired, a knife blade (not shown) may be reciprocated through knife channel 54 to cut tissue. Bleeding during tissue cutting is substantially reduced or eliminated due to the fact that tissue is sealed about the periphery of knife channel 54. That is, since tissue is sealed about the cutting path, little to no bleeding occurs upon subsequent advancement of a knife blade (not shown) along the cutting path to cut tissue.

Figure 6:
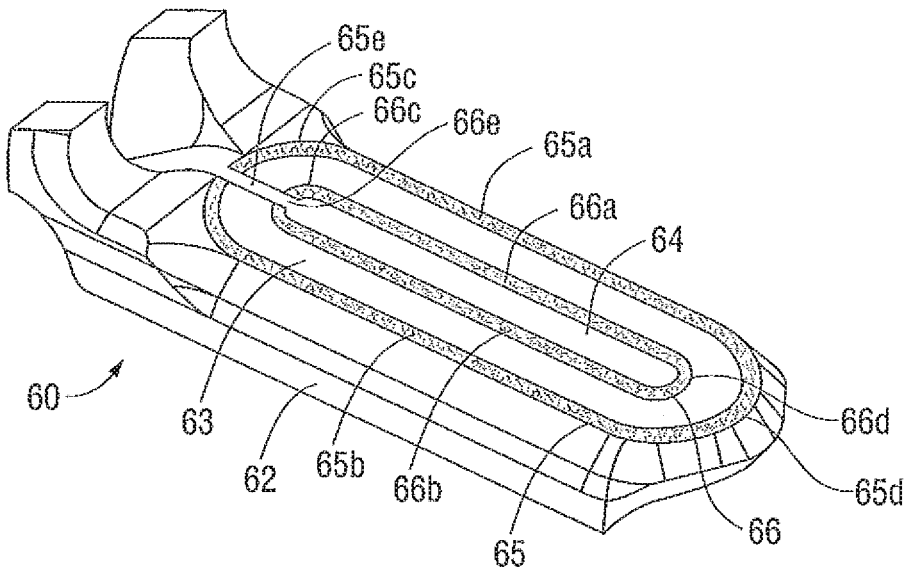
FIG. 6 is a top, perspective view of a jaw member of another end effector assembly provided in accordance with the present disclosure and configured for use with any of the above electrosurgical devices or any other suitable electrosurgical device.

Turning now to FIG. 6, the distal end of one of the jaw members of another end effector assembly 60 provided in accordance with the present disclosure is shown generally identified by reference numeral 62. End effector assembly 60 is similar to end effector assembly 50 (FIGS. 5A-5B) except that plates 65, 66 disposed on tissue-contacting surface 63 of jaw member 62 define generally oval-shaped configurations (as compared to the "U"-shaped configurations of plates 55, 56 of jaw member 52 (FIGS. 5A-5B). That is, each plate 65, 66 includes first and second longitudinal sections 65a, 65b and 66a, 66b, respectively, interconnected at their respective proximal ends via proximal curved sections 65c, 66c and at their respective distal ends via distal curved sections 65d, 66d. Proximal curved sections 65c, 66c are mirror-images of distal curved sections 65d, 66d, respectively, except that proximal curved sections 65c, 66c define interruptions 65e, 66e spanning knife channel 64 to enable reciprocation of a knife blade (not shown) into and through knife channel 64 of jaw member 62.

Referring to FIGS. 7-16, it has been found that an effective tissue seal, when utilizing transverse energy flow, is more readily achieved where tissue is heated such that boiling of tissue occurs first at the outer edges of the portion of tissue to be sealed. Boiling within tissue occurs when the temperature of tissue increases to a point where the vapor pressure of a component of tissue exceeds the ambient pressure within tissue. Boiling can be initiated at a particular location within tissue by raising the temperature at that location, by providing for a lower pressure at that location, or by utilizing both temperature and pressure differentials to ensure that the vapor pressure first exceeds the ambient pressure at that location. In other words, the two basic parameters that affect the boiling of tissue are: the temperature of tissue and the pressure within tissue. As such, the various embodiments of end effector assemblies detailed below with respect to FIGS. 7-16 are configured to control the temperature of tissue and/or the pressure applied to tissue so as to enable boiling to first occur at the outer edges of the portion of tissue to be sealed. Thus, these end effector assemblies are configured to facilitate formation of an effective tissue seal.

Figure 7:
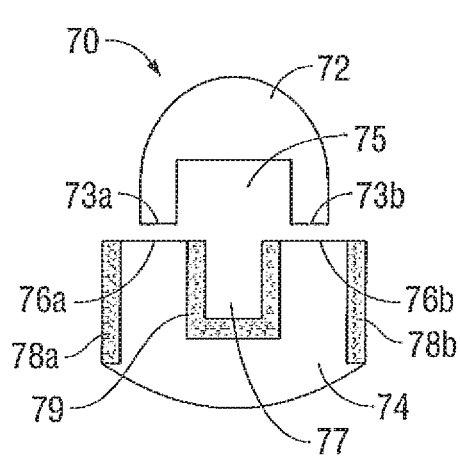
FIGS. 7-21 are transverse, cross-sectional views of various end effector assemblies provided in accordance with the present disclosure and configured for use with any of the above electrosurgical devices or any other suitable electrosurgical device.

With reference to FIG. 7, an end effector assembly 70 provided in accordance with the present disclosure is shown including first and second jaw members 72, 74, respectively. Jaw member 72 is formed from an electrically insulating material and defines a tissue-contacting surface divided into first and second tissue-contacting surface portions 73a, 73b by a knife channel 75 extending longitudinally through jaw member 72. Jaw member 74 is likewise formed from an electrically insulating material and defines a tissue-contacting surface divided into first and second tissue-contacting surface portions 76a, 76b by a knife channel 77 having a width smaller than that of knife channel 75. Jaw member 74 includes a pair of exterior electrodes, in the form of electrically-conductive plates 78a, 78b extending along the exterior lateral sides of jaw member 74 and positioned adjacent the exterior edges of tissue-contacting surface portions 76a, 76b of jaw member 74. Jaw member 74 further includes an interior electrode, in the form of an electrically-conductive plate 79 defining a "U"-shaped transverse cross-section, surrounding the interior of knife channel 77 and positioned adjacent the interior edges of tissue-contacting surface portions 76a, 76b of jaw member 74.

First and second tissue-contacting surface portions 73a, 73b of jaw member 72 define reduced widths as compared to respective first and second tissue-contacting surface portions 76a, 76b of jaw member 74 and are positioned closer towards plate 79 as compared to plates 78a, 78b. Further, upon approximation of jaw members 72, 74, as shown in FIG. 7, tissue is grasped between tissue-contacting surface portions 76a, 76b of jaw member 74 and the opposed portions of tissue-contacting surfaces 73a, 73b of jaw member 72. No portion of any of plates 78a, 78b, 79 is utilized to grasp tissue therebetween. Rather, due to the configuration of jaw members 72, 74, plates 78a, 78b, and 79 are disposed outside the tissue grasping areas defined between tissue-contacting surface portions 76a, 76b of jaw member 74 and the opposed portions of tissue-contacting surfaces 73a, 73b of jaw member 72, respectively.

In use, with tissue grasped between jaw members 72, 74, plates 78a, 78b are energized to a first electrical potential and plate 79 is energized to a second, different electrical potential to establish an electrical potential gradient therebetween. As such, energy is conducted between plates 78a, 78b and plate 79, and through tissue grasped within the tissue grasping areas in a generally transverse direction relative to jaw members 72, 74. Due to the above-described configuration of end effector assembly 70, the thermal path between plate 79 and the interior edges of tissue disposed within the tissue grasping areas is shorter than the thermal path between plates 78a, 78b and the exterior edges of tissue disposed within the tissue grasping areas. Thus, as energy is conducted between plates 78a, 78b and plate 79, relatively more heat is drawn away (i.e., relatively more conductive cooling is effected) from the interior edges of tissue disposed within the tissue grasping areas, while relatively less heat is drawn away (i.e., relatively less conductive cooling is effected) from plates 78a, 78b and the exterior edges of tissue disposed within the tissue grasping areas. As a result, with relatively less conductive cooling being effected at the exterior edges of tissue disposed within the tissue grasping areas, this tissue is heated faster and boils sooner as compared to the interior edges of tissue disposed within the tissue grasping areas. As noted above, this has been found to facilitate formation of an effective tissue seal.

Figure 8:
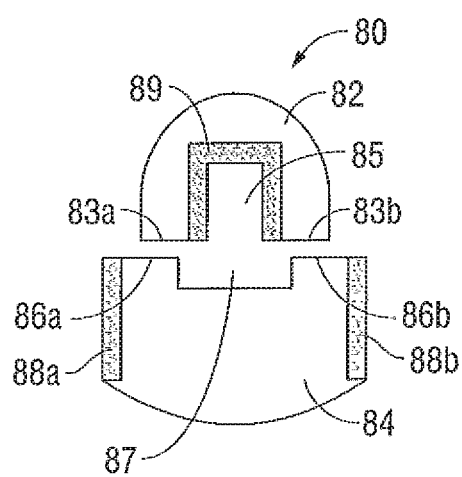

Referring to FIG. 8, another end effector assembly 80 provided in accordance with the present disclosure is shown including first and second jaw members 82, 84, respectively. End effector assembly 80 is similar to end effector assembly 70 (FIG. 7) except that, as detailed below, the internal electrode is disposed on the opposite jaw member. More specifically, jaw member 82 is formed from an electrically insulating material and defines a tissue-contacting surface divided into first and second tissue-contacting surface portions 83a, 83b by a knife channel 85 extending longitudinally through jaw member 82. An interior electrode in the form of an electrically-conductive plate 89 defining a "U"-shaped transverse cross-section surrounds the interior of knife channel 85 and is positioned adjacent the interior edges of tissue-contacting surface portions 83a, 83b of jaw member 82. Jaw member 84 is likewise formed from an electrically insulating material and defines a tissue-contacting surface divided into first and second tissue-contacting surface portions 86a, 86b by a recess 87 having a width greater than that of knife channel 85. Jaw member 84 further includes a pair of exterior electrodes, in the form of electrically-conductive plates 88a, 88b extending along the exterior lateral sides of jaw member 84 and positioned adjacent the exterior edges of tissue-contacting surface portions 86a, 86b of jaw member 84. Similarly as detailed above, plates 88a, 88b, and 89 are disposed outside the tissue grasping areas defined by jaw members 82, 84.

End effector assembly 80 is similar to end effector assembly 70 (FIG. 7) in that the thermal path between plate 89 and the interior edges of tissue disposed within the tissue grasping areas is shorter than the thermal path between plates 88a, 88b and the exterior edges of tissue disposed within the tissue grasping areas. Thus, as energy is conducted between plates 88a, 88b and plate 89, transversely across jaw members 82, 84, relatively more heat is drawn away from the interior edges of tissue disposed within the tissue grasping areas as compared to the exterior edges of tissue disposed within the tissue grasping areas such that the exterior edges of tissue disposed within the tissue grasping areas are heated faster and, thus, boil sooner. As noted above, this has been found to facilitate formation of an effective tissue seal.

Figure 9:
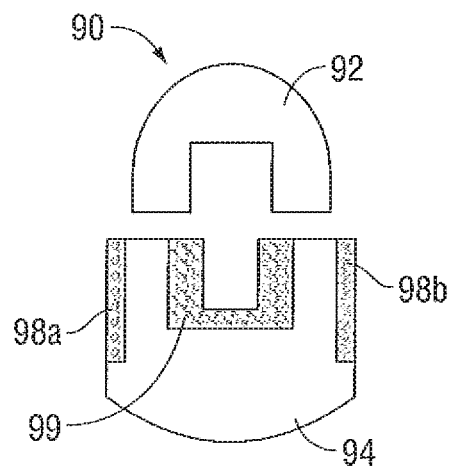
Figure 10:
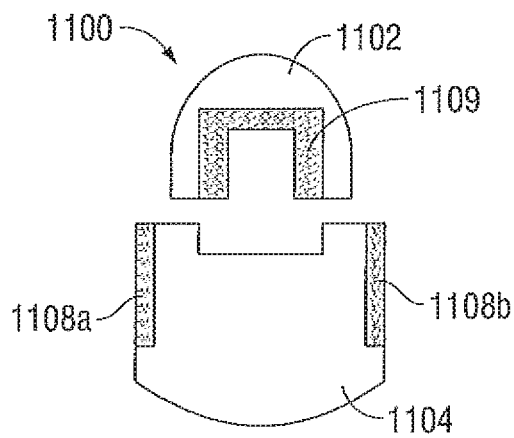

With reference to FIGS. 9-10, two end effector assemblies 90, 1100 provided in accordance with the present disclosure are shown each including first and second electrically insulating jaw members 92, 94 and 1102, 1104, respectively. End effector assembly 90 is similar to end effector assembly 70 (FIG. 7), while end effector assembly 1100 is similar to end effector assembly 80 (FIG. 8). However, end effector assemblies 90, 1100 differ from respective end effector assemblies 70, 80 (FIGS. 7-8, respectively) in that electrically-conductive plate 99 of jaw member 94 of end effector assembly 90 and electrically-conductive plate 1109 of jaw member 1102 of end effector assembly 1100 are partially overlapping with the tissue grasping areas defined by end effector assemblies 90, 1100, respectively. Electrically-conductive plates 98a, 98b of jaw member 94 of end effector assembly 90 and electrically-conductive plates 1108a, 1108b of jaw member 1104 of end effector assembly 1100 remain disposed outside the tissue grasping area of the respective end effector assembly 90, 1100.

As a result of the above-described configuration, and similar to end effector assemblies 70, 80 (FIGS. 7-8, respectively) as detailed above, the thermal path between plates 99, 1109 and the interior edges of tissue disposed within the tissue grasping areas of end effector assemblies 90, 1100 is shorter than the thermal path between plates 98a, 98b and 1108a, 1108b and the exterior edges of tissue disposed within the tissue grasping areas of end effector assemblies 90, 1100. Thus, as energy is conducted transversely between plates 98a, 98b and 1108a, 1108 and plates 99 and 1109, respectively, of end effector assemblies 90, 1100, the exterior edges of tissue disposed within the tissue grasping areas are heated faster and, thus, boil sooner than the interior edges of tissue disposed within the tissue grasping areas, facilitating formation of an effective tissue seal.

Additionally, the above-detailed configurations of end effector assemblies 90, 1100 (FIGS. 9-10, respectively), wherein plates 99, 1109 are partially overlapping with the tissue grasping areas defined by end effector assemblies 90, 1100 and wherein plates 98a, 98b and 1108a, 1108b are outside the tissue grasping areas defined by end effector assemblies 90, 1100, establishes a relatively higher pressure adjacent the interior edges of tissue disposed within the tissue grasping areas and a relatively lower pressure adjacent the exterior edges of tissue disposed within the tissue grasping areas. This relative pressure differential, in conjunction with the above-detailed configurations of end effector assemblies 90, 1100 (FIGS. 9-10, respectively), helps ensure that boiling of the exterior edges of tissue disposed within the tissue grasping areas occurs first.

In addition or as an alternative to varying the thermal path lengths to help ensure that tissue boiling occurs first at the exterior edges of tissue disposed within the tissue grasping areas, different materials having different heat sinking properties may be used to form the interior electrode(s) versus the exterior electrodes. For example, the interior electrode(s) may be formed from copper, while the exterior electrodes are formed from stainless steel. As such, since stainless steel is less effective at drawing heat away than is copper, the exterior edges of tissue disposed within the tissue grasping areas are heated and boil sooner. Other suitable materials having differing heat sinking properties may also be utilized in a similar fashion.

Figure 11:
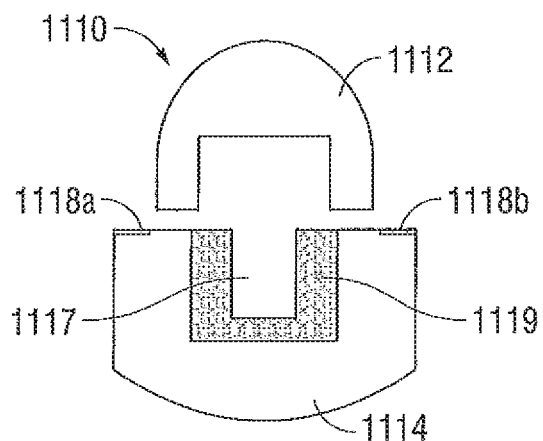
Figure 12:
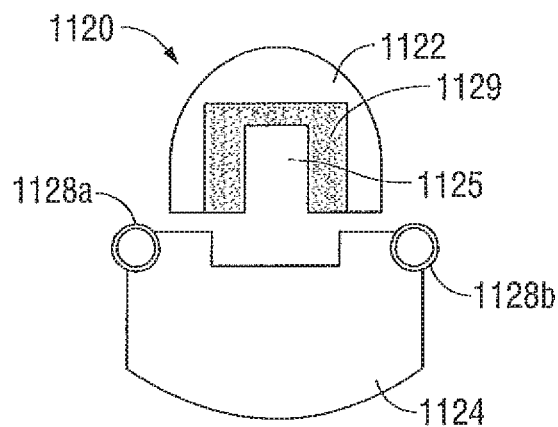
Figures 13, 14:
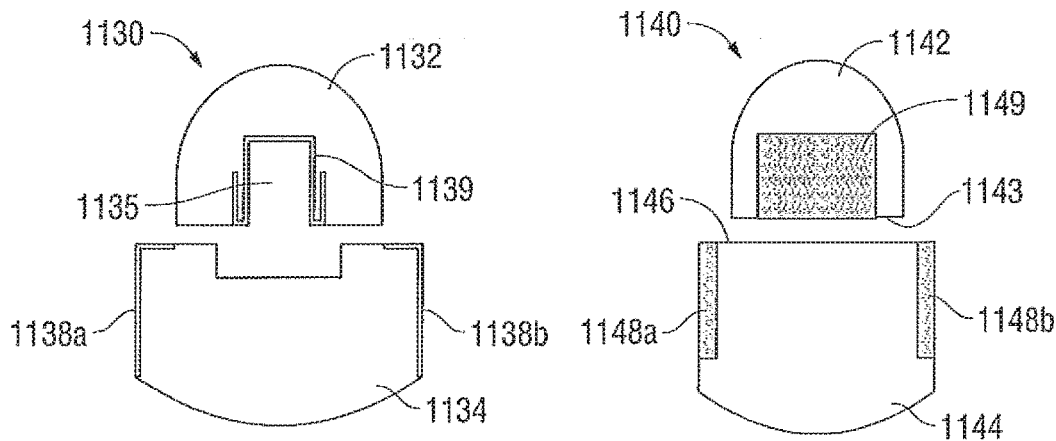

Turning to FIGS. 11-13, achieving tissue boiling first at the exterior edges of tissue disposed within the tissue grasping areas can also be accomplished, as an alternative to, or in addition to any of the above-detailed embodiments, by geometrically constructing the interior electrode and exterior electrodes (which are energized to conduct energy transversely therebetween) to have different heat sinking properties.

With reference to FIG. 11, another embodiment of an end effector assembly 1110 provided in accordance with the present disclosure is shown including first and second electrically insulating jaw members 1112, 1114, respectively. End effector assembly 1110 is similar to end effector assembly 90 (FIG. 9) and includes an interior electrode, in the form of an electrically-conductive plate 1119 defining a "U"-shaped transverse cross-section, disposed within knife channel 1117 of jaw member 1114, and a pair of exterior electrodes 1118a, 1118b disposed along the exterior lateral sides of jaw member 1114. Plate 1119 is partially overlapping with the tissue grasping areas defined between jaw members 1112, 1114, while electrodes 1118a, 1118b remain disposed outside the tissue grasping areas of end effector assembly 1110.

End effector assembly 1110 differs from end effector assembly 90 (FIG. 9) in that, rather both the interior and exterior electrodes being formed as plates having similar thicknesses, electrodes 1118a, 1118b are formed as thin strips of electrically-conductive material, while plate 1119 defines an increased thickness relative to electrodes 1118a, 1118b. As a result of electrodes 1118a, 1118b being thinner, electrodes 1118a, 1118b are less effective heat sinks as compared to the thicker plate 1119. Thus, the exterior edges of tissue disposed within the tissue grasping areas are heated faster and, thus, boil sooner, facilitating formation of an effective tissue seal.

End effector assembly 1120, as shown in FIG. 12, is similar to end effector assembly 1100 (FIG. 10) and includes first and second electrically insulating jaw members 1122, 1124, respectively. An interior electrode, in the form of an electrically-conductive plate 1129 defining a "U"-shaped transverse cross-section, is disposed within knife channel 1125 of jaw member 1122. A pair of exterior electrodes 1128a, 1128b are disposed along the exterior lateral sides of jaw member 1124. Plate 1129 is partially overlapping with the tissue grasping areas defined between jaw members 1122, 1124, while electrodes 1128a, 1128b remain disposed outside the tissue grasping areas of end effector assembly 1120.

End effector assembly 1120 differs from end effector assembly 1100 (FIG. 10) in that, rather both the interior and exterior electrodes being formed as plates having similar thicknesses, electrodes 1128a, 1128b are formed as hollow pipes of relatively thin, electrically-conductive material, while plate 1129 defines an increased thickness of electrically-conductive material relative to electrodes 1128a, 1128b. As a result of this configuration, electrodes 1128a, 1128b are less effective heat sinks as compared to the thicker, solid plate 1129. Thus, the exterior edges of tissue disposed within the tissue grasping areas are heated faster and, thus, boil sooner, facilitating formation of an effective tissue seal.

FIG. 13 illustrates another embodiment of an end effector assembly provided in accordance with the present disclosure and shown generally identified by reference numeral 1130. End effector assembly 1130 is similar to end effector assembly 80 (FIG. 8) and includes first and second electrically insulating jaw members 1132, 1134, respectively. Jaw member 1132 includes an electrode 1139 defining a "U"-shaped transverse cross-section disposed within knife channel 1135 thereof. Electrode 1139 is formed as a thin strip of electrically-conductive material that is folded back upon itself over at least a portion thereof. This folded configuration of electrode 1139 functions to increase the effective thickness of electrode 1139, thereby increasing the heat sinking properties of electrode 1139. Jaw member 1134 includes a pair of exterior electrodes 1138a, 1138b, in the form of thin strips of electrically-conductive material, that extend along the exterior lateral sides of jaw member 1134 and over the outer peripheral edges of the tissue-contacting surface of jaw member 1134. Exterior electrodes 1138a, 1138b, although bent at the edges of jaw member 1134, are not folded back upon themselves, and, thus, do not have the increased heat sinking properties of electrode 1139. Thus, the exterior edges of tissue disposed within the tissue grasping areas are heated faster and, thus, boil sooner, facilitating formation of an effective tissue seal.

Figures 15, 16:
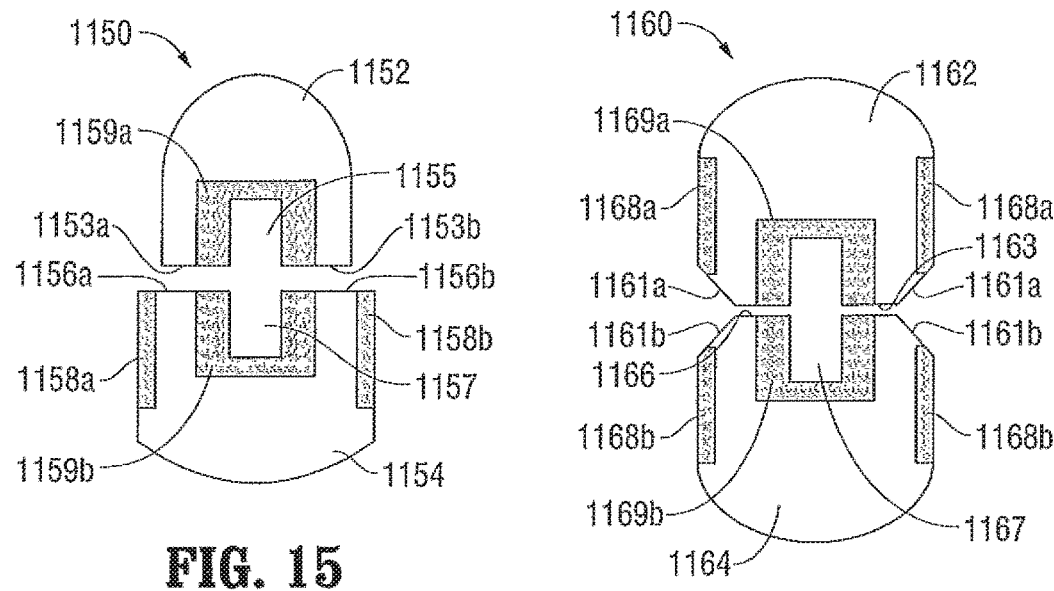

Referring to FIGS. 14-16, as noted above, establishing a relatively lower pressure adjacent the exterior edges of tissue disposed within the tissue grasping areas and a relatively higher pressure adjacent the grasped tissue and/or interior edges of tissue disposed within the tissue grasping areas facilitates heating and boiling of the exterior edges of tissue disposed within the tissue grasping areas first. The various embodiments of end effector assemblies detailed below with respect to FIGS. 14-16 are configured to achieve such a pressure differential, thus facilitating formation of an effective tissue seal.

With reference to FIG. 14, end effector assembly 1140 is shown including first and second electrically insulating jaw members 1142, 1144, each defining a tissue-contacting surface 1143, 1146. Although not shown, either or both of jaw members 1142, 1144 may define a knife channel extending longitudinally therealong, similarly as any of the previous embodiments. Jaw member 1142 includes an electrode 1149 defining an elongated block-shaped configuration. Electrode 1149 is disposed intermediately between the electrically insulating portions of jaw member 1142 and is recessed within jaw member 1142 so as to define a planar tissue-contacting surface 1143. Jaw member 1144, on the other hand, includes a pair of electrodes 1148a, 1148b formed as plates extending along the exterior lateral sides of jaw member 1144 and positioned adjacent the exterior edges of tissue-contacting surface 1146 of jaw member 1144. Electrode 1149 defines a greater width than both of electrodes 1148a, 1148b. Similarly as with the embodiments of FIGS. 7-13, jaw members 1142, 1144 are configured such that tissue-contacting surface 1146 of jaw member 1144 defines a greater width as compared to tissue-contacting surface 1143 of jaw member 1142. As a result of this configuration, electrode 1149 is positioned within the tissue grasping area of jaw members 1142, 1144, which is defined as the area between tissue-contacting surfaces 1143 and the opposed portion of tissue-contacting surface 1146, while electrodes 1148a, 1148b are disposed outside the tissue grasping area of end effector assembly 1140.

In use, tissue is initially grasped within the tissue grasping area, e.g., between tissue-contacting surfaces 1143 and the opposed portion of tissue-contacting surface 1146, such that electrode 1149 is positioned adjacent the interior section of tissue disposed within the tissue grasping area, while electrodes 1148a, 1148b are disposed outside the tissue grasping area adjacent the exterior edges of tissue disposed within the tissue grasping area. As a result of this configuration, the pressure applied to tissue in the vicinity of electrode 1149 is greater than the pressure applied to tissue in the vicinity of electrodes 1148a, 1148b. Thus, when energy is conducted between electrodes 1148a, 1148b and electrode 1149 (transversely relative to jaw members 1142, 1144) and through tissue disposed within the tissue grasping area, the above-noted pressure differential enables the exterior edges of tissue disposed at the exterior boundaries of the tissue sealing area to boil at a relatively lower temperature than the interior portions (as a result of the pressure differential therebetween) and, thus, to boil sooner, facilitating formation of an effective tissue seal.

Referring to FIG. 15, another end effector assembly 1150 provided in accordance with the present disclosure is shown including first and second jaw members 1152, 1154, respectively. Jaw member 1152 is formed from an electrically insulating material and defines a tissue-contacting surface divided into first and second tissue-contacting surface portions 1153a, 1153b by a knife channel 1155 extending longitudinally through jaw member 1152. A first interior electrode in the form of an electrically-conductive plate 1159a defining a "U"-shaped transverse cross-section surrounds the interior of knife channel 1155 and is positioned adjacent the interior edges of tissue-contacting surface portions 1153a, 1153b of jaw member 1152.

Jaw member 1154 is likewise formed from an electrically insulating material and defines a tissue-contacting surface divided into first and second tissue-contacting surface portions 1156a, 1156b by a knife channel 1157. Jaw member 1154 includes a pair of exterior electrodes, in the form of electrically-conductive plates 1158a, 1158b extending along the exterior lateral sides of jaw member 1154 and positioned adjacent the exterior edges of tissue-contacting surface portions 1156a, 1156b of jaw member 1154. Jaw member 1154 further includes a second interior electrode, in the form of an electrically-conductive plate 1159b defining a "U"-shaped transverse cross-section, surrounding the interior of knife channel 1157 and positioned adjacent the interior edges of tissue-contacting surface portions 1156a, 1156b of jaw member 1154. Similarly as above, electrodes 1158a, 1158b are disposed outside the tissue grasping area of end effector assembly 1150.

In use, tissue is initially grasped between jaw members 1152, 1154. That is, tissue is grasped within tissue grasping areas defined between the surfaces formed by tissue-contacting surface portions 1153a, 1153b and electrode 1159, and the surfaces formed by tissue-contacting surface portions 1156a, 1156b and electrode 1159b. However, as noted above, electrodes 1158a, 1158b are disposed outside the tissue grasping area. As a result of this configuration, the pressure applied to tissue in the vicinity of electrodes 1159a, 1159b is greater than the pressure applied to tissue in the vicinity of electrodes 1158a, 1158b. Thus, when energy is conducted between electrodes 1158a, 1158b and electrodes 1159a, 1159b (transversely relative to jaw members 1152, 1154) and through tissue grasped between jaw members 1152, 1154, heat is conducted towards the exterior edges of tissue disposed within the tissue grasping areas such that the exterior edges of tissue disposed within the tissue grasping areas boil at a lower temperature and, thus, sooner (as a result of the lower pressure), facilitating formation of an effective tissue seal.

FIG. 16 illustrates another end effector assembly 1160 provided in accordance with the present disclosure. End effector assembly 1160 includes first and second jaw members 1162, 1164 defining tissue-contacting surfaces 1163, 1166, respectively, divided by respective knife channels 1165, 1167. Jaw members 1162, 1164 each further define chamfered exterior edges 1161a, 1161b which interface between tissue-contacting surfaces 1163, 1166 and the respective exterior lateral sides of jaw members 1162, 1164. Either or both jaw members 1162, 1164 includes an interior electrode 1149a, 1149b defining a "U"-shaped transverse cross-section configuration and disposed within the respective knife channel 1165, 1167 thereof. Further, each jaw member 1162, 1164 includes a pair of exterior electrodes, in the form of electrically-conductive plates 1168a, 1168b extending along the exterior lateral sides of jaw members 1162, 1164, respectively. Chamfered exterior edges 1161a, 1161b are positioned adjacent plates 1168a, 1168b, respectively, and interconnect plates 1168a, 1168b with respective tissue-contacting surfaces 1163, 1166, respectively. Plates 1168a, 1168b may further include chamfered surfaces corresponding to chamfered exterior edges 1161a, 1161b so as to define a continuous, planar chamfered surface at the edges of jaw members 1162, 1164, as shown in FIG. 16.

In use, tissue is initially grasped between jaw members 1162, 1164. That is, tissue is grasped within tissue grasping areas defined between the surfaces formed by the divided portions of tissue-contacting surface 1163 and electrode 1169a, and the surfaces formed by the divided portions of tissue contacting surface 1166 and electrode 1169b. Due to the chamfered exterior edges 1161a, 1161b of jaw members 1162, 1164, plates 1168a, 1168b are further spaced-apart from one another as compared to tissue-contacting surfaces 1163, 1166. As a result, plates 1168a, 1168b exert a reduced pressure on the exterior edges of tissue disposed within the tissue grasping areas as compared to the pressure applied to the interior edges of tissue disposed within the grasping areas. Thus, when energy is conducted between electrodes 1168a, 1156b and electrodes 1169a, 1169b (transversely relative to jaw members 1162, 1164) and through tissue disposed within the grasping areas, heat is conducted towards the exterior edges of tissue disposed within the grasping areas such that the exterior edges of tissue disposed within the grasping areas boil at a lower temperature and, thus, sooner (as a result of the lower pressure), facilitating formation of an effective tissue seal.

Referring to FIGS. 17-21, as detailed above, it is desirable to provide an end effector assembly defining a tissue grasping area having a total width of less than about 8 mm or, more particularly, less than about 6 mm for use to seal tissue using transverse energy flow. Such a configuration also provides the benefit of being able to access small areas with the body endoscopically. However, providing such small jaw members difficulties in manufacturing. That is, the trade-off between providing sufficiently small structures and providing sufficient strength. The various embodiments of end effector assemblies detailed below with respect to FIGS. 17-21 achieved a desirable balance between size and strength. The jaw members of these end effector assemblies are manufactured by molding a polymeric material (forming the body of the jaw member), e.g., a biocompatible plastic, about the sheet metal electrodes (forming the electrodes of the jaw member) and sheet metal support members, if provided, although other suitable manufacturing techniques are also contemplated.

Figure 17:
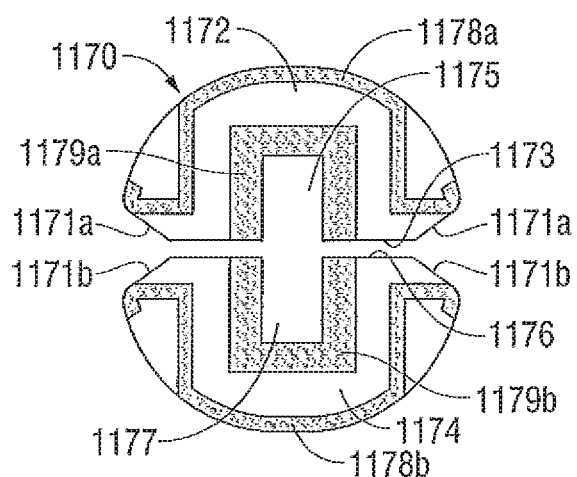

With reference to FIG. 17, an end effector assembly 1170 provided in accordance with the present disclosure is shown including first and second jaw members 1172, 1174, respectively. Jaw members 1172, 1174 define mirror image configurations of one another, although it is also contemplated that one of jaw members be provided with electrodes and the other jaw member simply provide an electrically insulating tissue-contacting surface for grasping tissue between jaw members 1172, 1174.

First and second jaw members 1172, 1174 of end effector assembly 1170 are formed from an electrically insulating polymeric material, e.g., a biocompatible plastic, or other suitable electrically insulating material and define tissue-contacting surfaces 1173, 1176, respectively, divided by respective knife channels 1175, 1177. Jaw members 1172, 1174 each further define chamfered exterior edges 1171a, 1171b, similarly as detailed above with respect to end effector assembly 1160 (FIG. 16), although other configurations are also contemplated. Each jaw member 1172, 1174 includes an interior electrode 1179a, 1179b in the form of a relatively thick piece of sheet metal bent to define a "U"-shaped transverse cross-section configuration and disposed within the respective knife channel 1175, 1177 of the jaw member 1172, 174, respectively. Each jaw member 1172, 1174 further includes an exterior electrode 1178a, 1178b, in the form of a relatively thin piece of sheet metal that extends along the exterior lateral sides of jaw members 1172, 1174, respectively. Exterior electrodes 1178a, 1178b are further routed through the respective jaw members 1172, 1174 and extend along an outer back surface (opposite the tissue-contacting surface) of the respective jaw members 1172, 1174. This configuration adds strength to jaw members 1172, 1174 and also enables a single piece of sheet metal to form both of the exterior electrodes 1178a, 1178b of the jaw member 1172, 1174, respectively. The ends of exterior electrodes 1178a, 1178b are bent adjacent the exterior lateral sides of jaw members 1172, 1174. Such a configuration provides an increased exposed surface area of exterior electrodes 1178a, 1178b in the vicinity of chamfered exterior edges 1171a, 1171b. In use, end effector assembly 1170 functions similarly to end effector assembly 1160 (FIG. 16), detailed above, and provides similar advantages with respect to tissue sealing using transverse energy flow.

Figure 18:
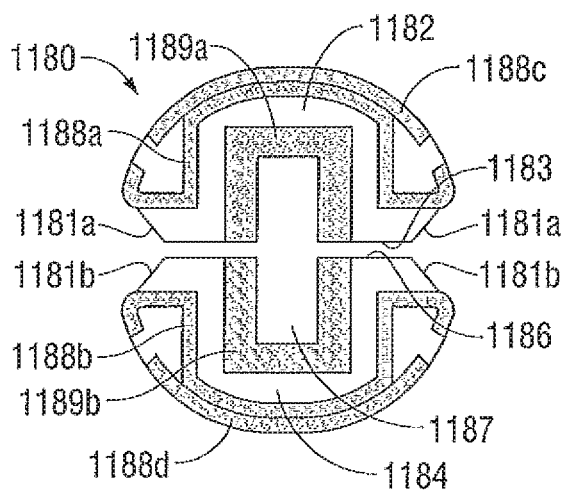

End effector assembly 1180, shown in FIG. 18, is similar to end effector assembly 1170 (FIG. 17) and generally includes first and second jaw members 1182, 1184, each defining a tissue-contacting surface 1183, 1186 divided by a knife channel 1185, 1187 and including a chamfered exterior edge 1181a, 1181b, an interior electrode 1189a, 1189b; and an exterior electrode 1188a, 1188b. However, end effector assembly 1180 differs from end effector assembly 1170 (FIG. 17) in that jaw members 1182, 1184 of end effector assembly 1180 each further includes a support member 1188c, 1188d, in the form of a relatively thin sheet of metal, disposed on the outer back surface of the respective jaw member 1182, 1184. More specifically, support members 1188c, 1188d are disposed in abutting relation with and are positioned on the outwardly-facing surfaces of the portions of electrodes 1188a, 1188b that extend along the outer back surfaces of respective jaw members 1182, 1184. Support members 1188c, 1188d provide added structural strength to jaw members 1182, 1184, while the ends of support members 1188c, 1188d are spaced-apart from the ends of exterior electrodes 1188a, 1188b so as not to interfere with the heating of tissue adjacent exterior electrodes 1188a, 1188b. The use of end effector assembly 1180 is similar to that of end effector assembly 1160 (FIG. 16), detailed above, and provides similar advantages.

Figure 19:
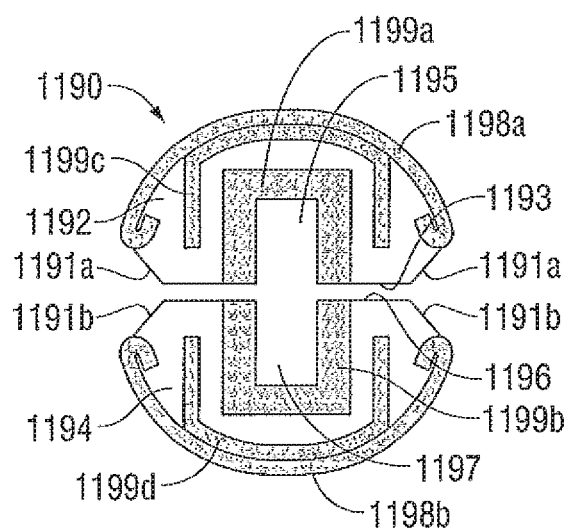

Turning to FIG. 19, another end effector assembly 1190 provided in accordance with the present disclosure is shown including first and second jaw members 1192, 1194, respectively. End effector assembly 1190 is similar to end effector assemblies 1170, 1180 (FIGS. 17-18, respectively). Jaw members 1192, 1194 of end effector assembly 1190, similarly as detailed above, each define a tissue-contacting surface 1193, 1196 divided by a knife channel 1195, 1197 and include a chamfered exterior edge 1191a, 1191b; an interior electrode 1199a, 1199b; and an exterior electrode 1198a, 1198b. Exterior electrodes 1198a, 1198b extend about the entire outer back surface of the respective jaw members 1192, 1194, and are bent at the ends thereof adjacent chamfered exterior edges 1191a, 1191b of jaw members 1192, 1194.

Either or both of jaw members 1192, 1194 of end effector assembly 1190 may further include a support member 1199c, 1199d disposed therein in the form of a piece of sheet metal bent to define a "U"-shaped transverse cross-section configuration. Support members 1199c, 1199d extend along the outer back surfaces of the respective jaw members 1192, 1194, interiority of exterior electrodes 1198a, 1198b, respectively. The crossbar portions of the "U"-shaped support members 1199c, 1199d abut exterior electrodes 1198a, 1198b. Further, support members 1199c, 1199d generally surround but are spaced-apart from respective interior electrodes 1199a, 1199b. The use of end effector assembly 1190 is similar to that of end effector assembly 1160 (FIG. 16), detailed above, and provides similar advantages.

Figure 20:
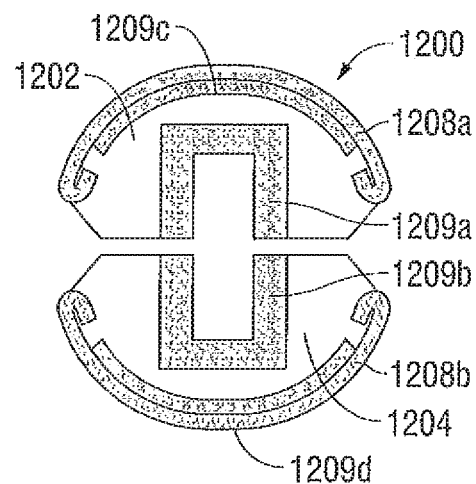

Referring to FIG. 20, another embodiment of an end effector assembly provided in accordance with the present disclosure is shown generally identified as end effector assembly 1200. End effector assembly 1200 is similar to end effector assembly 1190 (FIG. 19) and generally includes first and second jaw members 1202, 1204 each including an interior electrode 1209a, 1209b and an exterior electrode 1208a, 1208b. End effector assembly 1200 may further include any of the features of end effector assembly 1190 (FIG. 19), detailed above. However, end effector assembly 1200 differs from end effector assembly 1190 (FIG. 19) in that support members 1209c, 1209d do not define "U"-shaped configurations but, rather, simply extend along the outer back surfaces of the respective jaw members 1202, 1204 to provide additional structural support. The ends of support members 109c, 1209d are spaced apart-from the ends of exterior electrodes 1208a, 1208b so as not to interfere with the heating of tissue adjacent exterior electrodes 1208a, 1208b. The use of end effector assembly 1200 is similar to that of end effector assembly 1160 (FIG. 16), detailed above, and provides similar advantages.

Figure 21:
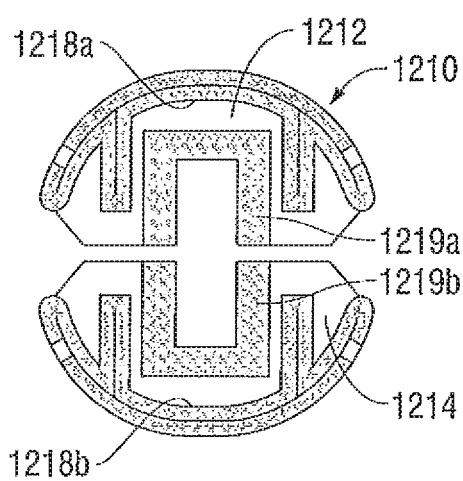

With reference to FIG. 21, another end effector assembly 1210 provided in accordance with the present disclosure is shown. End effector assembly 1210 is similar to end effector assembly 1180 (FIG. 18) and includes first and second jaw members 1212, 1214, each including an interior electrode 1219a, 1219b, an exterior electrode 1218a, 1218b, as well as any or all of the other features detailed above with respect to end effector assembly 1180 (FIG. 18). End effector assembly 1210 differs from end effector assembly 1180 (FIG. 18) in that exterior electrodes 1218a, 1218b of jaw members 1212, 1214 of end effector assembly 1210 each include folded sections positioned on either side of and spaced-apart from respective interior electrodes 1219a, 1219b. These folded sections of exterior electrodes 1218a, 1218b are disposed within jaw members 1212, 1214 and act as vertical structural supports for jaw members 1212, 1214 without affecting the use of end effector assembly 1210. Such use is similar to that of end effector assembly 1160 (FIG. 16), detailed above, and provides similar advantages.

With respect to any of the above embodiments, the jaw members may be constructed so as to define a total tissue grasping area (e.g., the cumulative total of the widths of the areas between which tissue is grasped and, ultimately, sealed) of equal to or less than about 8 mm or, even further, equal to or less than about 6 mm. It has been found that a tissue grasping area having a total width equal to or below these thresholds promotes formation of an effective tissue seal in that the tissue seal defines a total seal width (cumulative of both seals, in embodiments where two seals are established) less than about 8 mm or, further, less than about 6 mm.

Various energy control and/or feedback algorithms may be utilized in conjunction with any of the above-detailed embodiments of end effector assemblies for sealing tissue using transverse energy flow. In one implementation, energy may be supplied to the electrodes for conduction through tissue using a constant voltage amplitude. This energy is continuously supplied until the impedance through tissue reduces the current flow through tissue to essentially zero (or a pre-set minimum threshold), at which time the heating of tissue is essentially complete. Thereafter, the supply of energy may be cut off. It has been found that tissue is effectively sealed before this near stoppage in current flow occurs. As such, using this algorithm helps ensure that energy has been provided for a sufficient length of time to form an effective tissue seal. In some implementations, the supply of energy to the electrodes may continue even after the above-noted near stoppage in current flow has occurred, e.g., for an additional 0.25 seconds, to help ensure that tissue has been effectively sealed.

In other implementations, rather than supplying a constant voltage, varying or multiple voltage algorithms are provided. For example, energy may be supplied to the electrodes at an initial voltage until a pre-determined condition or threshold is met. Thereafter, the voltage is stepped-up to an increased voltage to complete the tissue seal. Suitable pre-determined conditions or thresholds include a minimum current threshold (which may be equal to the almost zero current flow threshold noted above), a minimum current rate of change, an impedance threshold, an impedance rate of change, passage of a pre-determined length of time, etc. Additional voltage increase "steps" may be provided, wherein each step-up occurs once a re-determined condition or threshold associated therewith is met.

With respect to end effector assemblies including a mechanical knife mechanisms for cutting sealed tissue, and particularly with respect to those end effector assemblies having reduced-sized jaw members, it has been found that re-energizing the electrodes after the sealing process has been completed and the mechanical knife reciprocated through the jaw members, helps ensure that the tissue seal remains effective and has not been compromised by the knife. Thus, a so-called "insurance" activation may be provided at the completion of tissue cutting. The algorithm, voltages, and/or other parameters used in this insurance activation may be similar to or different from those used in the regular activation phase.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly for an electrosurgical device, the end effector assembly comprising:
    first and second jaw members movable relative to one another between a spaced-apart position and an approximated position, each jaw member including an opposed tissue-contacting surface, the opposed tissue-contacting surfaces cooperating to define a tissue grasping area for grasping tissue therebetween when the jaw members are moved to the approximated position, the first jaw member including:
        an electrically-insulating body defining an outer back surface and an opposed surface, the opposed surface forming part of the tissue-contacting surface of the first jaw member;
        an interior electrode coupled to the electrically-insulating body, at least a portion of the interior electrode forming part of the tissue-contacting surface of the first jaw member; and
        an exterior electrode including:
            a first portion extending along the outer back surface of the electrically-insulating body;
            a second portion disposed adjacent the opposed surface of the electrically-insulating body; and
            a third portion interconnecting the first and second portions to one another and extending through the electrically-insulating body, wherein the interior and exterior electrodes are configured to conduct energy through tissue grasped between the first and second jaw members and within the tissue grasping area to seal tissue grasped within the tissue grasping area.

2. The end effector assembly according to claim 1, wherein the exterior electrode extends, in sequence, from the outer back surface, through the electrically-insulating body, and to a position adjacent the opposed surface of the electrically-insulating body.

3. The end effector assembly according to claim 1, wherein the opposed surface of the electrically-insulating body includes at least one chamfered exterior lateral side having the second portion of the exterior electrode disposed thereon.

4. The end effector assembly according to claim 1, wherein the interior electrode is thicker than the exterior electrode.

5. The end effector assembly according to claim 1, wherein the exterior electrode is formed from sheet metal.

6. The end effector assembly according to claim 1, wherein the electrically-insulating body defines a longitudinally-extending knife channel, the interior electrode being disposed within the knife channel.

7. The end effector assembly according to claim 6, wherein the knife channel and the inner electrode each have a generally "U"-shaped configuration.

8. The end effector assembly according to claim 1, wherein the first jaw member further includes an electrically-conductive support member disposed in contact with the exterior electrode.

9. The end effector assembly according to claim 8, wherein at least a portion of the electrically-conductive support member is disposed in abutting relation with an outwardly-facing surface of the first portion of the exterior electrode.

10. The end effector assembly according to claim 8, wherein first and second ends of the electrically-conductive support member are positioned adjacent respective first and second ends of the exterior electrode.

11. An end effector assembly for an electrosurgical device, the end effector assembly comprising:
    first and second jaw members movable relative to one another between a spaced-apart position and an approximated position, each jaw member including an opposed tissue-contacting surface, the opposed tissue-contacting surfaces cooperating to define a tissue grasping area for grasping tissue therebetween when the jaw members are moved to the approximated position, the first jaw member including:
        an electrically-insulating body defining an outer back surface and an opposed surface that forms part of the tissue-contacting surface of the first jaw member;

an interior electrode coupled to the electrically-insulating body, at least a portion of the interior electrode forming part of the tissue-contacting surface of the first jaw member; and an exterior electrode including:
- a back portion extending along the outer back surface of the electrically-insulating body;
- a pair of first and second lateral portions extending from opposing sides of the back portion and through the electrically-insulating body; and
- a pair of first and second end portions extending from the respective pair of first and second lateral portions, wherein each of the pair of first and second end portions is at least partially exposed to ambient conditions and disposed adjacent the opposed surface of the electrically-insulating body.

12. The end effector assembly according to claim 11, wherein the pair of first and second lateral portions of the exterior electrode couple the pair of first and second end portions with the back portion.

13. The end effector assembly according to claim 11, wherein the exterior electrode extends, in sequence, from the outer back surface, through the electrically-insulating body, and to a position adjacent the opposed surface of the electrically-insulating body.

14. The end effector assembly according to claim 11, wherein each of the pair of first and second end portions of the exterior electrode includes a segment bent away from the tissue-contacting surface of the first jaw member.

15. The end effector assembly according to claim 11, wherein the opposed surface of the electrically-insulating body includes a pair of first and second chamfered exterior lateral sides having the pair of first and second end portions of the exterior electrode respectively disposed thereon.

16. The end effector assembly according to claim 11, wherein the electrically-insulating body defines a longitudinally-extending knife channel, the interior electrode being disposed within the knife channel.

17. The end effector assembly according to claim 16, wherein the knife channel and the inner electrode each have a generally "U"-shaped configuration.

18. The end effector assembly according to claim 11, wherein the first jaw member further includes an electrically-conductive support member disposed in contact with the exterior electrode.

19. The end effector assembly according to claim 18, wherein at least a portion of the the electrically-conductive support member and is disposed in abutting relation with an outwardly-facing surface of the back portion of the exterior electrode.

20. The end effector assembly according to claim 18, wherein first and second ends of the electrically-conductive support member are positioned adjacent the respective first and second end portions of the exterior electrode.

* * * * *